(12) United States Patent
Gruber et al.

(10) Patent No.: US 6,417,193 B1
(45) Date of Patent: Jul. 9, 2002

(54) METHODS FOR INHIBITING MRP1

(75) Inventors: Joseph M Gruber, Brownsburg; Bryan H Norman, Indianapolis, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/646,074

(22) PCT Filed: Apr. 7, 1999

(86) PCT No.: PCT/US99/07343

§ 371 (c)(1),
(2), (4) Date: Sep. 13, 2000

(87) PCT Pub. No.: WO99/51227

PCT Pub. Date: Oct. 14, 1999

Related U.S. Application Data

(60) Provisional application No. 60/081,077, filed on Apr. 8, 1998.

(51) Int. Cl.[7] .................... A61K 31/443; A61K 31/444; C07D 498/04
(52) U.S. Cl. .......................................... 514/293; 546/83
(58) Field of Search .............................. 546/83; 514/293

(56) References Cited

U.S. PATENT DOCUMENTS

| 5,717,092 A | 2/1998 | Armistead et al. .......... 544/129 |
| 5,744,485 A | 4/1998 | Zelle et al. .................. 514/318 |

OTHER PUBLICATIONS

Caplus 114:206988 English abstract Roschger Peter et al , Liebigs Ann. Chem. 1991, vol. 4 pp. 401–403.*
W. Steinschifter, et al., Synthesis of Oxazolo [4,5–c]quinolones by Themolytic Degradatrion of 4–Azido–2 (1H)–quinolones [1], *J. Heterocyclic Chem.*, 31, pp. 1647–1652, (1994).

* cited by examiner

Primary Examiner—Alan L. Rotman
Assistant Examiner—Rita Desai
(74) Attorney, Agent, or Firm—Kirby W. Lee; Elizabeth A. Dawalt

(57) ABSTRACT

The present invention relates to a compound of formula (I) which is useful for inhibiting resistant neoplasms where the resistance is conferred in part or in total by MRP1.

6 Claims, No Drawings

METHODS FOR INHIBITING MRP1

This application is the U.S. National Stage filling of PCT/US99/07343, filed Apr. 7, 1999, which claims the benefit of U.S. Provisional Application Ser. No. 60/081,077, filed on Apr. 8, 1998.

Along with surgery and radiotherapy, chemotherapy continues to be an effective therapy for many cancers. In fact, several types of cancer are now considered to be curable by chemotherapy and include Hodgkin's disease, large cell lymphoma, acute lymphocytic leukemia, testicular cancer and early stage breast cancer. Other cancers such as ovarian cancer, small cell lung and advanced breast cancer, while not yet curable, are exhibiting positive response to combination chemotherapy.

One of the most important unsolved problems in cancer treatment is drug resistance. After selection for resistance to a single cytotoxic drug, cells may become cross resistant to a whole range of drugs with different structures and cellular targets, e.g., alkylating agents, antimetabolites, hormones, platinum-containing drugs, and natural products. This phenomenon is known as multidrug resistance (MDR). In some types of cells, this resistance is inherent, while in others, such as small cell lung cancer, it is usually acquired.

Such resistance is known to be multifactorial and is conferred by at least two proteins: the 170 kDa P-glycoprotein (MDR1) and the more recently identified 190 kDa multidrug resistance protein (MRP1). Although both MDR1 and MRP1 belong to the ATP-binding cassette superfamily of transport proteins, they are structurally very different molecules and share less than 15% amino acid homology. Despite the structural divergence between the two proteins, by 1994 there were no known consistent differences in the resistance patterns of MDR1 and MRP1 cell lines. However, the association, or lack thereof, of MRP1 and resistance to particular oncolytics is known. See Cole, et. al., "Pharmacological Characterization of Multidrug Resistant MRP-transfected Human Tumor Cells", *Cancer Research*, 54: 5902–5910, 1994. Doxorubicin, daunorubicin, epirubicin, vincristine, and etoposide are substrates of MRP1, i.e., MRP1 can bind to these oncolytics and redistrubute them away from their site of action, the nucleus, and out of the cell. Id. and Marquardt, D., and Center, M.S., *Cancer Research*, 52:3157, 1992.

Doxorubicin, daunorubicin, and epirubicin are members of the anthracycline class of oncolytics. They are isolates of various strains of Streptomyces and act by inhibiting nucleic acid synthesis. These agents are useful in treating neoplasms of the bone, ovaries, bladder, thyroid, and especially the breast. They are also useful in the treatment of acute lymphoblastic and myeloblastic leukemia, Wilm's tumor, neuroblastoma, soft tissue sarcoma, Hodgkin's and non-Hodgkin's lymphomas, and bronchogenic carcinoma.

Vincristine, a member of the vinca alkaloid class of oncolytics, is an isolate of a common flowering herb, the periwinkle plant (*Vinca rosea* Linn). The mechanism of action of vincristine is still under investigation but has been related to the inhibition of microtubule formation in the mitotic spindle. Vincristine is useful in the treatment of acute leukemia, Hodgkin's disease, non-Hodgkin's malignant lymphomas, rhabdomyosarcoma, neuroblastoma, and Wilm's tumor.

Etoposide, a member of the epipodophyllotoxin class of oncolytics, is a semisynthetic derivative of podophyllotoxin. Etoposide acts as a topoisomerase inhibitor and is useful in the therapy of neoplasms of the testis, and lung.

It is presently unknown what determines whether a cell line will acquire resistance via a MDR1 or MRP1 mechanism. Due to the tissue specificity of these transporters and/or in the case where one mechanism predominates or is exclusive, it would be useful to have a selective inhibitor of that one over the other. Furthermore, when administering a drug or drugs that are substrates of either protein, it would be particularly advantageous to co-administer an agent that is a selective inhibitor of that protein. It is, therefore, desirable to provide compounds which are selective inhibitors of MDR1 or MRP1.

The present invention relates to a compound of formula I:

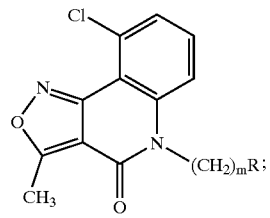

where:
m is an integer from 1 to 6;
R is $COR^1$, amino, NH-Pg, or $NHCOR^2$;
$R^1$ is hydroxy, $C_1$–$C_6$ alkoxy, or $NR^3R^4$;
Pg is an amino protecting group;
$R^2$ is $C_1$–$C_6$ alkyl, substituted $C_1$–$C_4$ alkyl, aryl, substituted aryl, $(CH_2)_n$-heterocycle, $(CH_2)_n$-substituted heterocycle;
$R^3$ is independently at each occurrence hydrogen or $C_1$–$C_6$ alkyl;
$R^4$ is $C_1$–$C_6$ alkyl, norbornan-2-yl, aryl, substituted aryl, $CH_2CH(CH_3)$phenyl, $(CH_2)_n$heterocycle, or $(CH_2)_n$-substituted heterocycle; and
n is 0, 1, or 2; or a pharmaceutical salt or solvate thereof.

The present invention further relates to a method of inhibiting MRP1 in a mammal which comprises administering to a mammal in need thereof an effective amount of a compound of formula I, or a pharmaceutical salt or solvate thereof.

In another embodiment, the present invention relates to a method of inhibiting a resistant neoplasm, or a neoplasm susceptible to resistance in a mammal which comprises administering to a mammal in need thereof an effective amount of a compound of formula I, or a pharmaceutical salt or solvate thereof, in combination with an effective amount of an oncolytic agent.

The present invention also relates to a pharmaceutical formulation comprising a compound of formula I, or a pharmaceutical salt or solvate thereof, in combination with one or more oncolytics, pharmaceutical carriers, diluents, or excipients therefor.

The current invention concerns the discovery that a select group of compounds, those of formula I, are selective inhibitors of multidrug resistant protein (MRP1) and are thus useful in treating MRP1 conferred multidrug resistance (MDR) in a resistant neoplasm and a neoplasm susceptible to resistance.

The terms "inhibit" as it relates to MRP1 and "inhibiting MRP1" refer to prohibiting, alleviating, ameliorating, halting, restraining, slowing or reversing the progression of, or reducing MRP1's ability to redistribute an oncolytic away from the oncolytic's site of action, most often the neoplasm's nucleus, and out of the cell.

As used herein, the term "effective amount of a compound of formula I" refers to an amount of a compound of the present invention which is capable of inhibiting MRP1. The term "effective amount of an oncolytic" refers to an amount of oncolytic capable of inhibiting a neoplasm, resistant or otherwise.

The term "inhibiting a resistant neoplasm, or a neoplasm susceptible to resistance" refers to prohibiting, halting, restraining, slowing or reversing the progression of, reducing the growth of, or killing resistant neoplasms and/or neoplasms susceptible to resistance.

The term "resistant neoplasm" refers to a neoplasm which is resistant to chemotherapy where that resistance is conferred in part, or in total, by MRP1. Such neoplasms include, but are not limited to, neoplasms of the bladder, bone, breast, lung(small-cell), testis, and thyroid and also includes more particular types of cancer such as, but not limited to, acute lymphoblastic and myeloblastic leukemia, Wilm's tumor, neuroblastoma, soft tissue sarcoma, Hodgkin's and non-Hodgkin's lymphomas, and bronchogenic carcinoma.

A neoplasm which is "susceptible to resistance" is a neoplasm where resistance is not inherent nor currently present but can be conferred by MRP1 after chemotherapy begins. Thus, the methods of this invention encompass a prophylactic and therapeutic administration of a compound of formula I.

The term "chemotherapy" refers to the use of one or more oncolytics where at least one oncolytic is a substrate of MRP1. A "substrate of MRP1" is an oncolytic that binds to MRP1 and is redistributed away from the oncolytics site of action, (the neoplasm's nucleus) and out of the cell, thus, rendering the therapy less effective.

The terms "treat" or "treating" bear their usual meaning which includes preventing, prohibiting, alleviating, ameliorating, halting, restraining, slowing or reversing the progression, or reducing the severity of MRP1 derived drug resistance in a multidrug resistant tumor.

In the general formulae of the present document, the general chemical terms have their usual meanings. For example, the term "$C_1$–$C_4$ alkyl" refers to methyl, ethyl, propyl, isopropyl, cyclopropyl, butyl, cyclobutyl, s-butyl, and t-butyl. The term "$C_1$–$C_6$ alkyl" refers to a monovalent, straight, branched, or cyclic saturated hydrocarbon containing from 1 to 6 carbon atoms and includes $C_1$–$C_4$ alkyl groups. In addition, $C_1$–$C_6$ alkyl also includes, but is not limited to, cyclopentyl, pentyl, hexyl, cyclohexyl, and the like.

The term "aryl" refers to phenyl, benzyl, and napthyl.

The term "heterocycle" refers to a monovalent, saturated, unsaturated, or aromatic mono cyclic or fused ring system of 5 to 7 or 8 to 10 total atoms, respectively, containing from 1 to 3 heteroatoms selected independently from oxygen, sulfur, and nitrogen. Examples of heterocyclic groups include, but are not limited to, furanyl, indolyl, thiophenyl, isoxazolyl, all partially saturated or fully saturated analogues thereof, e.g., tetrahydrofuran, and the like, wherein the point of attachment to the heterocycle is at any position on the ring available for substitution.

The term "substituted heterocycle" refers to a heterocycle ring substituted 1 or 2 times independently with a $C_1$–$C_6$ alkyl, halo, benzyl, phenyl, trifluoromethyl, or an oxo group.

The term "substituted aryl" refers to a phenyl, benzyl, and napthyl group, respectively, substituted from 1 to 5 times independently with halo, hydroxy, trifluoromethyl, $N(R^1)_2$, NH-Pg, $C_1$–$C_4$ alkoxy, benzyloxy, $CO_2R^1$, $SO_2NH_2$, trifluoromethoxy, or nitro.

The term "substituted $C_1$–$C_4$ alkyl" refers to a $C_1$–$C_4$ alkyl group where 1 to 3 hydrogens have been replaced by the same halide, e.g., trifluoromethyl.

The term "halo" or "halide" refers to fluoro, chloro, bromo, or iodo.

The term "$C_1$–$C_4$ alkoxy" refers to a $C_1$–$C_4$ alkyl group attached through an oxygen atom.

The term "amino protecting group" as used in this specification refers to a substituent(s) of the amino group commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivatize amino group is stable to the condition of subsequent reaction (s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by T. W. Greene, "Protective Groups in Organic Synthesis", John Wiley and Sons, New York, N.Y., 1991, Chapter 7 hereafter referred to as "Greene". A preferred amino protecting group is t-butyloxycarbonyl.

The term "carbonyl activating group" refers to a substituent of a carbonyl that renders that carbonyl prone to nucleophilic addition. Suitable activating groups are those which have a net electron withdrawing effect on the carbonyl. Such groups include, but are not limited to, alkoxy, aryloxy, nitrogen containing aromatic heterocycles, or amino groups such as oxybenzotriazole, imidazolyl, nitrophenoxy, pentachlorophenoxy, N-oxysuccinimide, N,N'-dicyclohexylisoure-O-yl, N-hydroxy-N-methoxyamino, and the like; acetates, formates, sulfonates such as methanesulfonate, ethanesulfonate, benzenesulfonate, or p-toluenylsulfonate, and the like; and halides especially chloride, bromide, or iodide.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical Salts", *J. Pharm. Sci.*, 66:1, 1977. Typical pharmaceutical salts include those salts prepared by reaction of the compounds of formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

Examples of pharmaceutical acid addition salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, ethanesulfonate, propanesulfonate, naphthalene-1-sulfonate, napththalene-2-sulfonate, mandelate, and the like of a compound of formula I.

Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of formula I.

The term "solvate" represents an aggregate that comprises one or more molecules of the solute, such as a formula I compound, with one or more molecules of solvent.

The term "suitable solvent" refers to a solvent which is inert to the ongoing reaction and sufficiently solubilizes the reactants to effect the desired reaction. Examples of suitable solvents include but are not limited to, dichloromethane, chloroform, 1,2-dichloroethane, diethyl ether, acetonitrile, ethyl acetate, 1,3-dimethyl-2-imidazolidinone, tetrahydrofuran, dimethylformamide, toluene, chlorobenzene, dimethylsulfoxide, mixtures thereof, and the like.

The term "carbonyl activating reagent" refers to a reagent that converts the carbonyl of a carboxylic acid group to one that is more prone to nucleophilic addition and includes, but is not limited to, such reagents as those found in "The Peptides", Gross and Meienhofer, Eds., Academic Press (1979), Ch. 2 and M. Bodanszky, "Principles of Peptide Synthesis", $2_{nd}$ Ed., Springer-Verlag Berlin Heidelberg, 1993, hereafter referred to as "The Peptides" and "Peptide Synthesis" respectively. Specifically, carbonyl activating reagents include nucleophilic sources of a halogen such as, thionyl bromide, thionyl chloride, oxalyl chloride, and the like; alcohols such as nitrophenol, pentachlorophenol, and the like; amines such as N-hydroxy-N-methoxyamine and the like; acid halides such as acetic, formic, methanesulfonic, ethanesulfonic, benzenesulfonic, or p-tolenesulfonic acid halide, and the like; and compounds such as 1,1'-carbonyldiimidazole, benzotriazole, imidazole, N-hydroxysuccinimide, dicyclohexylcarbodiimide, and the like.

The term "suitable thermodynamic base" refers to a base which acts as a proton trap for any protons which may be produced as a byproduct of the desired reaction or to a base which provides a reversible deprotonation of an acidic substrate and is reactive enough to effect the desired reaction without significantly effecting any undesired reactions. Examples of thermodynamic bases include, but are not limited to, carbonates, bicarbonates, and hydroxides (e.g., lithium, sodium, or potassium carbonate, bicarbonate, or hydroxide), tri-($C_1$–$C_4$ alkyl)amines, or aromatic nitrogen containing heterocycles (e.g., pyridine).

While all of the compounds of the present invention are useful, certain of the compounds are particularly interesting and are preferred. The following listing sets out several groups of preferred compounds, formulations, and methods. It will be understood that each of the listings may be combined with other listings to create additional groups of preferred embodiments.
a) m is an integer from 2 to 6;
b) R is amino;
c) R is t-butyloxycarbonylamino;
d) R is trifluoroacetylamino;
e) R is 3,4,5-trimethoxybenzoylamino;
f) R is carboxy;
g) R is 3,4,5-trimethoxyanilinylcarboxy;
h) R is 3,4,5-trimethoxybenzylaminylcarboxy;
i) The compounds of the Examples section;
j) The compound is a pharmaceutical salt;
k) The compound is the hydrochloride salt;
l) The method where the mammal is a human;
m) The method where the oncolytic(s) is selected from: doxorubicin, daunorubicin, epirubicin, vincristine, and etoposide;
n) The method where the neoplasm is of the Wilm's type, bladder, bone, breast, lung(small-cell), testis, or thyroid or the neoplasm is associated with acute lymphoblastic and myeloblastic leukemia, neuroblastoma, soft tissue sarcoma, Hodgkin's and non-Hodgkin's lymphomas, or bronchogenic carcinoma; and
o) The formulation where the oncolytic(s) is selected from the group: doxorubicin, daunorubicin, epirubicin, vincristine, and etoposide.

The compounds of the present invention can be prepared by a variety of procedures, some of which are illustrated in the Schemes below. The particular order of steps required to produce the compounds of formula I is dependent upon the particular compound being synthesized, the starting compound, and the relative lability of the substituted moieties.

Compounds of formula I may be prepared from compounds of formula II as illustrated in Scheme 1 below where R and m are as described supra.

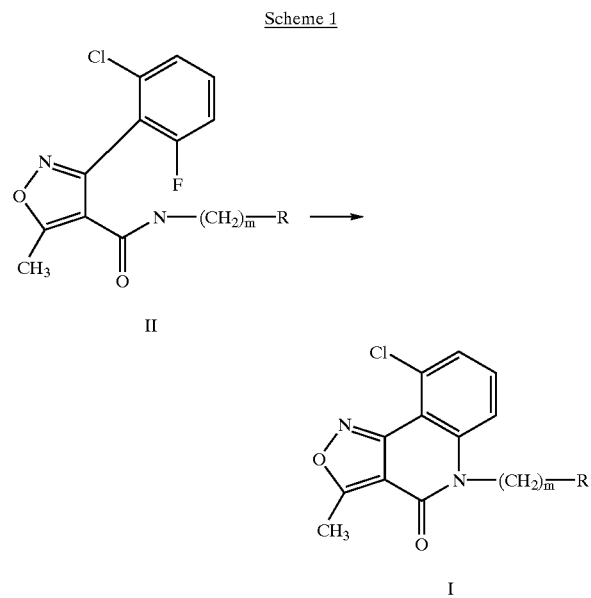

Compounds of formula I may be prepared by dissolving or suspending a compound of formula II in a suitable solvent and adding a suitable thermodynamic base. Typically a preferred and convenient solvent is dimethylformamide. Usually a convenient and preferred thermodynamic base is sodium hydroxide added as a 2N solution in methanol. The reactants are typically combined at room temperature and the resulting solution is typically allowed to react for from 30 minutes to about 18 hours. Preferably, the mixture is stirred about 1 to about 10 hours, and is most preferably stirred for about 3.5 hours to about 7 hours. The base is typically employed in a large molar excess, usually in about a 4 to about an 8 molar excess relative to the compound of formula II. Preferably, about a 5 to about a 7 molar excess is typically employed. Certain intermediates, discussed below, of compounds of formula I may also be prepared by the method discussed above.

Any hydroxy or amino protecting groups found in the cyclized compound of formula I may optionally be removed as taught in Greene to provide the free amino or free hydroxy compounds of formula I. Preferred choices of protecting groups and methods for their removal may be found in the Preparations and Examples sections below.

Compounds of formula I, where R is $COR^1$ may also be prepared from compounds of formula I(a) as illustrated in Scheme 2 below where $R^5$ is a carboxy activating group, $R^6$ is $C_1-C_6$ alkoxy, or $NR^3R^4$ and m is as described supra.

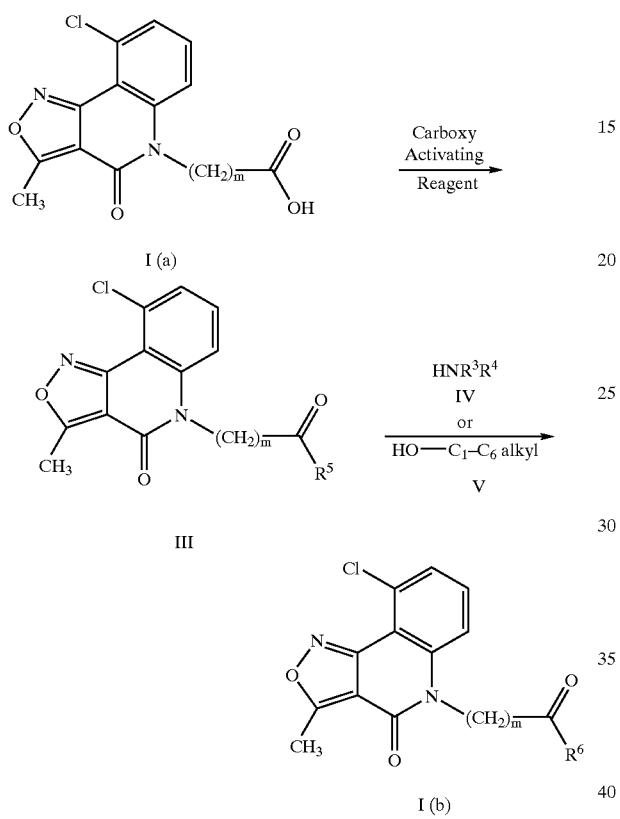

The compounds of formula I(b) where $R^6$ is $C_1-C_6$ alkoxy, i.e., esters, may be prepared by methods very well known in the chemical arts. For instruction on the conversion of activated carboxylic acids to esters see, e.g., Larock, "Comprehensive Organic Transformations", pgs. 978–979, VCH Publishers, New York, N.Y., 1989, hereafter referred to as "Larock". Alternatively, these compounds of formula I(b) may be prepared directly from the acids of formula I(a) as taught in Larock at pages 966–972.

Compounds of formula I where R is amino or $NHCOR^2$ may be prepared from compounds of formula I(c) as illustrated in Scheme 3 below where m, Pg, $R^2$, and $R^5$ are as described supra.

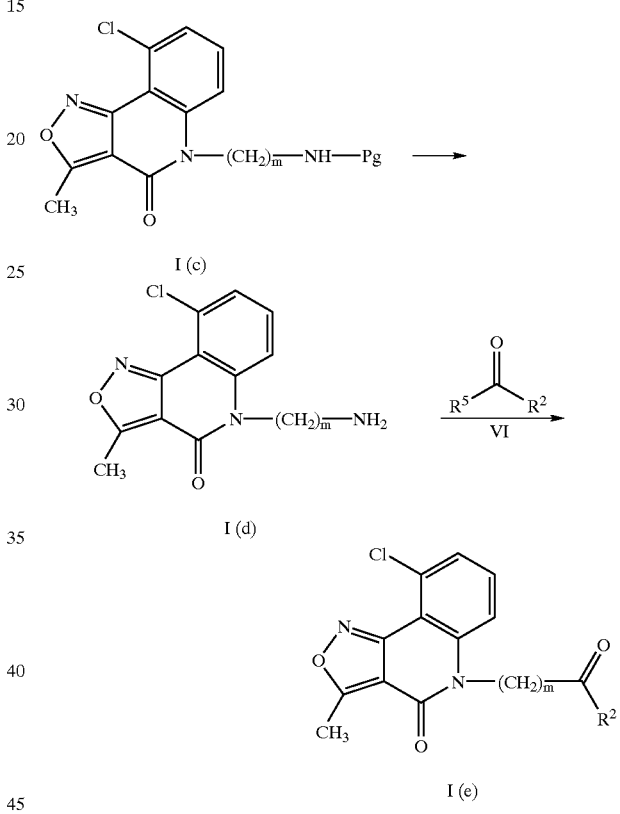

Compounds of formula I(a), prepared as described in Scheme 1, may be converted to other compounds of the invention. For example, acids of formula I(a) may be activated to form the activated carboxylic acids of formula III by methods well known in the chemical arts. See, e.g., The Peptides, Peptide Synthesis, and the Examples and Preparations sections below.

Compounds of formula I(b) may then be prepared by dissolving or suspending a compound of formula III in a suitable solvent, optionally in the presence of a suitable thermodynamic base, and adding an amine of formula IV. Typically a preferred and convenient solvent is dichloromethane. Preferred bases are triethylamine and piperidinylmethylpolystyrene resin. The amine is typically employed in a molar excess. For example, about a 1.5 to about a 3 molar excess, relative to the compound of formula III, is usually employed. About 1.8 to about 2.2 molar excess is typically preferred. The reaction is usually performed in a temperature range of about 0° C. to about the reflux temperature of the solvent for from 10 minutes to 18 hours. Preferably, the reaction is performed at about 15° C. to about 40° C. for 5 minutes to about 2.5 hours.

Alternatively, the compound of formula I(a) may be activated and the addition of a compound of formula IV may be performed in a one pot process as described in Examples 26 and 38 below.

Compounds of formula I(c) may be converted to other compounds of the invention. For example, a compound of formula I(c) may have its protecting group removed as taught in Greene or in the Examples section which follows to form a compound of formula I(d). These compounds of formula I(d) may then be converted to other compounds of the invention as well. For example, a compound of formula I(d) dissolved or suspended in a suitable solvent, optionally in the presence of a thermodynamic base, may be treated with a compound of formula VI to provide a compound of formula I(e). Typically a preferred and convenient solvent is dimethylformamide or a mixture of dichloromethane and dimethylformamide. When a base is employed, triethylamine or N-methylmorpholine is typically a preferred base. Furthermore, when a base is employed, the base and compound of formula VI are typically employed in a stoichiometric to large molar excess. For example a 1.0 to 4 molar excess, relative to the compound of formula I(d), is generally employed. When a base is not employed, the compound of formula VI is typically employed in a relatively larger stoichiometric excess. It is preferred to perform the reaction in the presence of a base with from about 1.8 to about 2.2 equivalents of a compound of formula VI. The reaction is usually performed at a temperature range of about 0° C. to about the reflux temperature of the solvent for from 10 minutes to 24 hours. Preferably, the reaction is performed at about 15° C. to about 40° C. for from 4 to about 18 hours.

The pharmaceutical salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The starting materials for the processes of the present invention may be obtained by a number of routes. For example, compounds of formula II, I(a), and I(c) may be prepared according to the route shown in Scheme 4 where m and R are as described supra.

Scheme 4

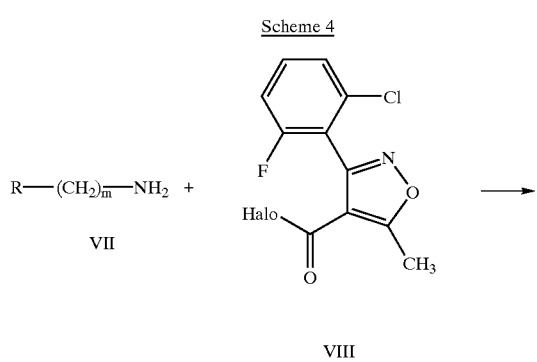

VII

-continued

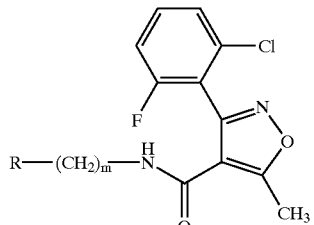

II

Compounds of formula II may be prepared by dissolving or suspending a compound of formula VII in a suitable solvent and adding a compound of formula VIII and a suitable thermodynamic base. Dichloromethane is a convenient solvent and is typically preferred. Triethylamine is usually a preferred thermodynamic base. This amide forming reaction is also preferably run in the presence of dimethylamino pyridine (DMAP). The compound of formula VIII is typically and preferably employed in an equimolar amount, relative to the compound of formula VII, but a slight excess (about a 0.05 to about 0.15 molar excess) is acceptable. The thermodynamic base is typically employed in a slight molar excess. For example, about a 1.01 to about a 1.2 molar excess, relative to the compound of formula VII, is typically employed. About a 1.05 to about 1.15 molar excess is generally preferred. The DMAP is employed in a catalytic fashion. For example, about 5 molar percent to about 15 molar percent, relative to the compound of formula VII, is typically employed. A 10 molar percent is usually preferred.

Although the transformations described in Schemes 2 and 3 may be performed before the cyclization described in Scheme 1 to provide the compounds of formula VII with a fully elaborated R substituent, it is preferred to perform these reactions after the cyclization. Thus, preferred starting materials for the reaction of Scheme 1 and 4 are the compounds of formula II and VII where R is NH-Pg or $COR^1$ where $R^1$ is $C_1$–$C_6$ alkoxy. Furthermore, if the reaction of Scheme 1 is performed with a compound of formula II where R is $COR^1$ and $R^1$ is $C_1$–$C_6$ alkoxy, under the conditions described for the cyclization, that ester will be cleaved to the acid, i.e., will give the compounds of formula I(a).

Compounds of formula IV, V, VI, VII, and VIII are known in the art and, to the extent not commercially available, are readily synthesized by standard procedures commonly employed in the art.

The optimal time for performing the reactions of Schemes 1–4 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds of formula I(d) and II are preferably isolated and purified before their use in subsequent reactions. These compounds may crystallize out of the reaction solution during their formation and then be collected by filtration, or the reaction solvent may be removed by extraction, evaporation, or decantation. These intermediate and final products of formula I may be further purified, if desired by common techniques such as recrystallization or chromatography over solid supports such as silica gel or alumina.

The following Preparations and Examples are provided to better elucidate the practice of the present invention and should not be interpreted in any way as to limit the scope of same. Those skilled in the art will recognize that various modifications may be made while not departing from the spirit and scope of the invention. All publications mentioned in the specification are indicative of the level of those skilled in the art to which this invention pertains. The terms and abbreviations used in the instant Preparations and Examples have their normal meanings unless otherwise designated. For example "°C.", "N", "mmol", "g", "mL", "M", "IR", "MS(FD)",and "MS(IS)" refer to degrees Celsius, normal or normality, millimole or millimoles, gram or grams, milliliter or milliliters, molar or molarity, infra red spectrometry, field desorption mass spectrometry, and ion spray mass spectrometry respectively. In addition, the absorption maxima listed for the IR spectra are only those of interest and not all of the maxima observed.

PREPARATIONS

Preparation 1

N-t-Butyloxycarbonyl-N'-(3-[2-Chloro-6-Fluorophenyl]-5-Methylisoxazol-4-oyl)-1,2-Diaminoethane N-t-butyloxycarbonyl-1,2-diaminoethane (355 mg, 2.22 mmol), dimethylaminopyridine (27 mg, 0.222 mmol), and triethylamine (247 mg, 2.44 mmol) were combined in 5 mL of dry dichloromethane. 3-(2-Chloro-6-fluorophenyl)-5-methylisoxazol-4-oyl chloride (607 mg, 2.22 mmol) was added in slowly. The reaction was stirred for 3 hours at room temperature under nitrogen. The reaction was diluted with ethyl acetate and water. The ethyl acetate was separated and washed three times each with 25 mL of 1N aqueous hydrochloric acid and brine, dried over sodium sulfate, filtered, and concentrated in vacuo. The residue was treated with hexanes to crystallize 794 mg of the title compound. (90%). EA calculated for: $C_{18}H_{21}N_3O_4ClF$: C, 54.34; H, 5.32; N, 10.56. Found: C, 54.30; H, 5.36; N, 10.44. MS(IS) m/z 398 (M+).

Preparation 2

N-t-Butyloxycarbonyl-N'-(3-[2-Chloro-6-Fluorophenyl]-5-Methylisoxazol-4-oyl)-1,3-Diaminopropane N-t-butyloxycarbonyl-1,3-diaminopropane (574 mg, 3.29 mmol) and 3-(2-chloro-6-fluorophenyl)-5-methylisoxazol-4-oyl chloride (903 mg, 3.29 mmol) were converted to 1.36 g of the title compound by the procedure of Preparation 1. (100%). EA calculated for: $C_{19}H_{23}N_3O_4ClF$: C, 55.41; H, 5.63; N, 10.20. Found: C, 55.17; H, 5.71; N, 9.99. MS(IS) m/z 412 (M+).

Preparation 3

N-t-Butyloxycarbonyl-N'-(3-[2-Chloro-6-Fluorophenyl]-5-Methylisoxazol-4-oyl)-1,4-Diaminobutane N-t-butyloxycarbonyl-1,4-diaminobutane (985 mg, 5.23 mmol) and 3-(2-chloro-6-fluorophenyl)-5-methylisoxazol-4-oyl chloride (1.43 g, 5.23 mmol) were converted to 2.23 g of the title compound by the procedure of Preparation 1 except that the reaction time was about 18 hours. (100%). EA calculated for: $C_{20}H_{25}N_3O_4ClF$: C, 56.41; H, 5.92; N, 9.87. Found: C, 56.12; H, 5.75; N, 9.67. MS(FD) m/z 426 (M+).

Preparation 4

N-t-Butyloxycarbonyl-N'-(3-[2-Chloro-6-Fluorophenyl]-5-Methylisoxazol-4-oyl)-1,5-Diaminopentane N-t-butyloxycarbonyl-1,5-diaminopentane (1.04 g, 5.14 mmol) and 3-(2-chloro-6-fluorophenyl)-5-methylisoxazol-4-oyl chloride (1.41 g, 5.14 mmol) were converted to 2.14 g of the title compound by the procedure of Preparation 1. (95%). MS(IS) m/z 412 (M+). IR(CHCl$_3$) 3496, 3012, 2936, 1708, 1663, 1611, 1510 cm$^{-1}$.

Preparation 5

N-t-Butyloxycarbonyl-N'-(3-[2-Chloro-6-Fluorophenyl]-5-Methylisoxazol-4-oyl)-1,6-Diaminohexane N-t-butyloxycarbonyl-1,6-diaminohexane hydrochloride salt (1.02 g, 4.03 mmol) and 3-(2-chloro-6-fluorophenyl)-5-methylisoxazol-4-oyl chloride (1.11 g, 4.03 mmol) were converted to 1.84 g of the title compound by the procedure of Preparation 1. (100%). EA calculated for: $C_{22}H_{29}N_3O_4ClF$: C, 58.21; H, 6.44; N, 9.26. Found: C, 57.97; H, 6.20; N, 9.43. MS(IS) m/z 454 (M+)

Preparation 6

Methyl-4-Aminobutanoate Hydrochloride

N-t-butyloxycarbonyl-4-aminobutanoic acid (1 g, 4.92 mmol) was dissolved in 10 mL of a freshly prepared mixture of hydrochloric acid and methanol (2.5 mL of acetyl chloride in 35 mL of methanol). The reaction was stirred for about 2 hours and then stripped down. The residue was taken up in ethyl acetate, washed three times each with aqueous sodium bicarbonate and brine, dried over sodium sulfate, and filtered and concentrated down leaving 708 mg of the title compound. (94%). EA calculated for $C_5H_{12}ClNO_2$: C, 39.10; H, 7.87; N, 9.12. Found: C, 38.89; H, 7.65; N, 8.94. MS(FD) m/z 118 (M+for free amine).

Preparation 7

Methyl-5-Aminopentanoate Hydrochloride

N-t-butyloxycarbonyl-5-aminopentanoic acid (1 g, 4.60 mmol) was converted to the title compound by the procedure of Preparation 6 to give 705 mg. (91%). EA calculated for $C_6H_{14}ClNO_2$: C, 42.99; H, 8.42; N, 8.36. Found: C, 43.02; H, 8.15; N, 8.18. MS(FD) m/z 132 (M+for free amine).

Preparation 8

Methyl-6-Aminohexanoate Hydrochloride

N-t-butyloxycarbonyl-6-aminohexanoic acid ;500 mg, 2.16 mmol) was converted to the title compound by the procedure of Preparation 6 to give 357 mg. (91%). EA calculated for $C_7H_{16}ClNO_2$: C, 46.28; H, 8.88; N, 7.71. Found: C, 46.04; H, 8.88; N, 7.51. MS(FD) m/z 146 (M+for free amine).

Preparation 9

Methyl-7-Aminoheptanoate Hydrochloride

N-t-butyloxycarbonyl-7-aminoheptanoic acid (1 g, 4.08 mmol) was converted to the title compound by the procedure of Preparation 6 to give 742 mg. (93%). EA calculated for $C_8H_{17}ClNO_2$: C, 49.10; H, 9.27; N, 7.16. Found: C, 49.10; H, 9.18; N, 7.03. MS(FD) m/z 160 (M+for free amine).

Preparation 10

Methyl-N-(3-[2-Chloro-6-Fluorophenyl]-5-Methylisoxazol-4-oyl)-4-Aminobutanoate

Methyl-4-aminobutanoate hydrochloride (668 mg, 4.34 mmol) and 3-(2-chloro-6-fluorophenyl)-5-methylisoxazol-4-oyl chloride (1.19 g, 4.35 mmol) were converted to 1.60 g of the title compound by the procedure of Preparation 1 except that the residue was not treated with hexanes. (100%). EA calculated for: $C_{16}H_{16}N_2O_4ClF$: C, 54.17; H, 4.55; N, 7.90. Found: C, 54.41; H, 4.58; N, 7.78. MS(FD) m/z 355 (M+).

Preparation 11

Methyl-N-(3-[2-Chloro-6-Fluorophenyl]-5-Methylisoxazol-4-oyl)-5-Aminopentanoate

Methyl-5-aminopentanoate hydrochloride (694 mg, 4.14 mmol) and 3-(2-chloro-6-fluorophenyl)-5-methylisoxazol-4-oyl chloride (1.24 g, 4.52 mmol) were converted to 1.36 g of the title compound by the procedure of Preparation 10. (100%). EA calculated for: $C_{17}H_{18}N_2O_4ClF$: C, 55.37; H, 4.92; N, 7.60. Found: C, 55.44; H, 5.00; N, 7.52. MS(FD) m/z 368 (M+).

Preparation 12

Methyl-N-(3-[2-Chloro-6-Fluorophenyl]-5-Methylisoxazol-4-oyl)-6-Aminohexanoate

Methyl-6-aminohexanoate hydrochloride (349 mg, 1.92 mmol) and 3-(2-chloro-6-fluorophenyl)-5-methylisoxazol-4-oyl chloride (527 mg, 1.92 mmol) were converted to 2.23 g of the title compound by the procedure of Preparation 10. (100%). EA calculated for: $C_{18}H_{20}N_2O_4ClF$: C, 56.48; H, 5.27; N, 7.32. Found: C, 56.66; H, 5.20; N, 7.07. MS(FD) m/z 382.2 (M+).

Preparation 13

Methyl-N-(3-[2-Chloro-6-Fluorophenyl]-5-Methylisoxazol-4-oyl)-7-Aminoheptanoate

Methyl-7-aminoheptanoate hydrochloride (733 mg, 3.75 mmol) and 3-(2-chloro-6-fluorophenyl)-5-methylisoxazol-4-oyl chloride (1.03 g, 3.75 mmol) were converted to 1.48 g of the title compound by the procedure of Preparation 10. (100%). EA calculated for: $C_{19}H_{22}N_2O_4ClF$: C, 57.51; H, 5.59; N, 7.06. Found: C, 57.78; H, 5.70; N, 6.80. MS(FD) m/z 396.1 (M+).

EXAMPLES

Example 1

1-(N-t-Butyloxycarbonyl-2-Aminoethyl)-Isoxazolo[3,4-c]-1,2-Dihydro-3-Methyl-6-Chloroquinolin-2-one N-t-Butyloxycarbonyl-N'-(3-(2-chloro-6-fluorophenyl)-5-methylisoxazol-4-oyl)ethylene-1,2-diamine (772 mg, 1.94 mmol) was dissolved in 10 mL of dry dimethylformamide and stirred under nitrogen at room temperature. Aqueous sodium hydroxide (5 mL) was added and the resulting solution was stirred for 4 hours. The reaction was partitioned between 50 mL of 1N aqueous hydrochloric acid and ethyl acetate. The ethyl acetate was washed three times with 25 mL of brine and dried over sodium sulfate. The solution was concentrated in vacuo to provide 721 mg of the title compound. (98%). EA calculated for $C_{15}H_{20}ClN_3O_4$: C, 57.22; H, 5.34; N, 11.12. Found: C, 57.21; H, 5.23; N, 10.97. MS(IS) m/z 376 (M−H).

Example 2

1-(N-t-Butyloxycarbonyl-3-Aminopropyl)-Isoxazolo[3,4-c]-1,2-Dihydro-3-Methyl-6-Chloroquinolin-2-one N-t-Butyloxycarbonyl-N'-(3-(2-chloro-6-fluorophenyl)-5-methylisoxazol-4-oyl)-1,3-diaminopropane (1.31 g, 3.18 mmol) was converted to 1.22 g of the title compound by the procedure of Example 1 except that reaction time was 6 hours. (99%). EA calculated for $C_{19}H_{22}ClN_3O_4$: C, 58.24; H, 5.66; N, 10.72. Found: C, 58.48; H, 5.52; N, 10.73. MS(IS) m/z 392 (M+).

Example 3

1-(N-t-Butyloxycarbonyl-4-Aminobutyl)-Isoxazolo[3,4-c]-1,2-Dihydro-3-Methyl-6-Chloroquinolin-2-one N-t-Butyloxycarbonyl-N'-(3-(2-chloro-6-fluorophenyl)-5-methylisoxazol-4-oyl)-1,4-diaminobutane (2.23 g, 5.23 mmol) was converted to 2.11 g of the title compound by the procedure of Example 1 except that after concentration, the residue was azeotroped with xylenes to remove residual dimethylformamide. (99%). EA calculated for $C_{20}H_{24}ClN_3O_4$: C, 59.19; H, 5.96; N, 10.35. Found: C, 58.71; H, 5.92; N, 9.96. MS(FD) m/z 405 (M+).

Example 4

1-(N-t-Butyloxycarbonyl-5-Aminopentyl)-Isoxazolo[3,4-c]-1,2-Dihydro-3-Methyl-6-Chloroquinolin-2-one N-t-Butyloxycarbonyl-N'-(3-(2-chloro-6-fluorophenyl)-5-methylisoxazol-4-oyl)-1,5-diamimopentane (2.11 g, 4.80 mmol) was converted to 1.13 g of the title compound by the procedure of Example 1 except that reaction time was 6 hours and, after concentration, the residue was recrystallized from dichloromethane:hexanes. (56%). EA calculated for $C_{21}H_{26}ClN_3O_4$: C, 60.07; H, 6.24; N, 10.01. Found: C, 60.07; H, 6.30; N, 10.11. MS(IS) m/z 420 (M+).

Example 5

1-(N-t-Butyloxycarbonyl-6-Aminohexyl)-Isoxazolo[3,4-c]-1,2-Dihydro-3-Methyl-6-Chloroquinolin-2-one N-t-Butyloxycarbonyl-N'-(3-(2-chloro-6-fluorophenyl)-5-methylisoxazol-4-oyl)-1,6-diamimohexane (1.84 g, 4.05 mmol) was converted to 1.45 g of the title compound by the procedure of Example 3. (82%). EA calculated for $C_{22}H_{28}ClN_3O_4$: C, 60.89; H, 6.50; N, 9.68. Found: C, 61.19; H, 6.33; N, 9.51. MS(IS) m/z 434.6 (M+).

Example 6

1-(2-Aminoethyl)-Isoxazolo[3,4-c]-1,2-Dihydro-3-Methyl-6-Chloroquinolin-2-one Trifluoroacetate 1-(N-t-Butyloxycarbonyl-2-aminoethyl)-isoxazolo[3,4-c]-1,2-dihydro-3-methyl-6-chloroquinolin-2-one (687 mg, 1.82 mmol) was dissolved in 10 mL of dichloromethane and trifluoroacetic acid (3 mL) was added. The mixture was stirred under nitrogen at room temperature for 2 hours. The solvents were removed and the residue was precipitated with ethyl acetate/hexanes to give 830 mg of the title compound. (100%). MS(FD) m/z 277 (M+ for free amine). IR(KBr) 3145, 1778, 1665, 1646, 1626 cm$^{-1}$.

Example 7

1-(3-Aminopropyl)-Isoxazolo[3,4-c]-1,2-Dihydro-3-Methyl-6-Chloroquinolin-2-one Trifluoroacetate 1-(N-t-Butyloxycarbonyl-3-aminopropyl)-isoxazolo[3,4-c]-1,2-dihydro-3-methyl-6-chloroquinolin-2-one (922 mg, 2.35 mmol) was converted to 837 mg of the title compound by the procedure of Example 6 except that reaction time was 3 hours. (88%). EA calculated for $C_{16}H_{15}ClF_3N_3O_4$: C, 47.36; H, 3.73; N, 10.36. Found: C, 47.44; H, 3.70; N, 10.34. MS(IS) m/z 292 (M+ for free amine).

Example 8

1-(4-Aminobutyl)-Isoxazolo[3,4-c]-1,2-Dihydro-3-Methyl-6-Chloroquinolin-2-one Trifluoroacetate 1-(N-t-Butyloxycarbonyl-4-aminobutyl)-isoxazolo[3,4-c]-1,2-dihydro-3-methyl-6-chloroquinolin-2-one (3.14 g, 7.75 mmol) was converted to 2.90 g of the title compound by the procedure of Example 7. (89%). EA calculated for $C_{17}H_{17}ClF_3N_3O_4$: C, 48.64; H, 4.08; N, 10.01. Found: C, 48.49; H, 3.95; N, 9.91. MS(IS) m/z 306 (M+ for free amine).

Example 9

1-(5-Aminopentyl)-Isoxazolo[3,4-c]-1,2-Dihydro-3-Methyl-6-Chloroquinolin-2-one Trifluoroacetate 1-(N-t-Butyloxycarbonyl-5-aminopentyl)-isoxazolo[3,4-c]-1,2-dihydro-3-methyl-6-chloroquinolin-2-one (1.08 g, 2.57 mmol) was converted to 1.01 g of the title compound by the procedure of Example 7. (56%). EA calculated for $C_{18}H_{19}ClF_3N_3O_4$: C, 49.84; H, 4.41; N, 9.69. Found: C, 50.08; H, 4.23; N, 9.69. MS(IS) m/z 320 (M+ for free amine).

Example 10

1-(6-Aminohexyl)-Isoxazolo[3,4-c]-1,2-Dihydro-3-Methyl-6-Chloroquinolin-2-one Trifluoroacetate 1-(N-t-Butyloxycarbonyl-6-aminohexyl)-isoxazolo[3,4-c]-1,2-dihydro-3-methyl-6-chloroquinolin-2-one (1.40 g, 3.23 mmol) was converted to 1.30 g of the title compound by the procedure of Example 7. (90%). EA calculated for $C_{19}H_{21}ClF_3N_3O_4$: C, 50.96; H, 4.73; N, 9.38. Found: C, 51.20; H, 4.62; N, 9.31. MS(IS) m/z 334 (M+ for free amine).

Example 11 and 12

1-(N-Trifluoroacetate-2-Aminoethyl)-Isoxazolo[3,4-c]-1,2-Dihydro-3-Methyl-6-Chloroquinolin-2-one and 1-(N-3,4,5-Trimethoxybenzoyl-2-Aminoethyl)-Isoxazolo[3,4-c]-1,2-Dihydro-3-Methyl-6-Chloroquinolin-2-one 1-(2-Aminoethyl)-isoxazolo[3,4-c]-1,2-dihydro-3-methyl-6-chloroquinolin-2-one trifluoroacetate (50 mg, 0.128 mmol) was suspended in 3 mL of dry dichloromethane and N-methylmorpholine (12.9 mg, 0.128 mmol) and 1 mL of dry dimethylformamide was added. The resulting solution was stirred under nitrogen at room temperature and 3,4,5-trimethoxybenzoyl chloride (59 mg, 0.255 mmol) was added and the resulting mixture was stirred for about 18 hours. The reaction was worked up by the addition of ethyl acetate and water. The ethyl acetate was separated and washed three times each with 25 mL of 1N aqueous hydrochloric acid, sodium bicarbonate, and brine. The ethyl acetate was dried over sodium sulfate and filtered. The ethyl acetate was removed and the residue was chromatographed (silica gel, 1:1 ethyl acetate:hexane) to give 21 mg of the trifluoroacetate amide title compounds and 12 mg of the benzoyl amide title compound. (20%). Trifluoroacetate amide: MS(IS) m/z 372 (M–H). Benzoyl amide: MS(IS) m/z 472 (M+).

Example 13 and 14

1-(N-Trifluoroacetate-3-Aminopropyl)-Isoxazolo[3,4-c]-1,2-Dihydro-3-Methyl-6-Chloroquinolin-2-one and 1-(N-3,4,5-Trimethoxybenzoyl-3-Aminopropyl)-Isoxazolo[3,4-c]-1,2-Dihydro-3-Methyl-6-Chloroquinolin-2-one 1-(3-Aminopropyl)-isoxazolo[3,4-c]-1,2-dihydro-3-methyl-6-chloroquinolin-2-one trifluoroacetate and 3,4,5-trimethoxybenzoyl chloride (0.9 equivalents) were converted to the title compounds by the procedure of Examples 11 and 12 to give 6 mg of the trifluoroacetate amide title compound and 48 mg of the benzoyl amide title compound. (65%). Trifluoroacetate amide: MS(IS) m/z 388 (M+). Benzoyl amide: MS(FD) m/z 485 (M+). IR(KBr) 3284, 1673, 1634, 1585, 1339 cm$^{-1}$.

Example 15

1-(N-3,4,5-Trimethoxybenzoyl-4-Aminobutyl)-Isoxazolo[3,4-c]-1,2-Dihydro-3-Methyl-6-Chloroquinolin-2-one 1-(4-Aminobutyl)-isoxazolo[3,4-c]-1,2-dihydro-3-methyl-6-chloroquinolin-2-one trifluoroacetate (75 mg, 0.179 mmol) was dissolved in 2 mL of dry dimethylformamide and stirred under nitrogen at room temperature. Triethylamine (54 mg, 0.537 mmol) was added and the solution turned purple. 3,4,5-Trimethoxybenzoyl chloride (62 mg, 0.268 mmol) was then added and the resulting mixture was stirred for about 18 hours. The reaction was diluted with ethyl acetate and washed three time each with 25 mL of 1N aqueous hydrochloric acid, aqueous sodium bicarbonate, and brine, dried over sodium sulfate, filtered, and concentrated. The residue was chromatographed (silica gel, ethyl acetate) and the appropriate fractions were recrystallized from dichloromethane to give 40 mg of the title compound. (45%). MS(IS) m/z 500 (M+). IR(KBr) 1674, 1634, 1597, 1585, 1501 cm$^{-1}$.

Example 16 and 17

1-(N-Trifluoroacetate-5-Aminopentyl)-Isoxazolo[3,4-c]-1,2-Dihydro-3-Methyl-6-Chloroquinolin-2-one and 1-(N-3,4,5-Trimethoxybenzoyl-5-Aminopentyl)-Isoxazolo[3,4-c]-1,2-Dihydro-3-Methyl-6-Chloroquinolin-2-one 1-(5-Aminopentyl)-isoxazolo[3,4-c]-1,2-dihydro-3-methyl-6-chloroquinolin-2-one trifluoroacetate and 3,4,5-trimethoxybenzoyl chloride (0.9 equivalents) were converted to the title compounds by the procedure of Examples 11 and 12 to give 0.7 mg of the trifluoroacetate amide title compound and 41 mg of the benzoyl amide title compound. (51%). Trifluoroacetate amide: MS(IS) m/z 416 (M+). Benzoyl amide: MS(FD) m/z 513 (M+). IR(KBr) 1667, 1629, 1597, 1580, 1500 cm$^{-1}$.

Example 18 and 19

1-(N-Trifluoroacetate-6-Aminohexyl)-Isoxazolo[3,4-c]-1,2-Dihydro-3-Methyl-6-Chloroquinolin-2-one
and
1-(N-3,4,5-Trimethoxybenzoyl-6-Aminohexyl)-Isoxazolo[3,4-c]-1,2-Dihydro-3-Methyl-6-Chloroquinolin-2-one 1-(6-Aminohexyl)-isoxazolo[3,4-c]-1,2-dihydro-3-methyl-6-chloroquinolin-2-one trifluoroacetate and 3,4,5-trimethoxybenzoyl chloride (0.9 equivalents) were converted to the title compounds by the procedure of Examples 11 and 12 to give 10.7 mg of the trifluoroacetate amide title compound and 36 mg of the benzoyl amide title compound. (45%). Trifluoroacetate amide: EA calculated for $C_{19}H_{19}ClF_3N_3O_3$: C, 53.09; H, 4.46; N, 9.78. Found: C, 53.34; H, 4.37; N, 9.72. MS(IS) m/z 430 (M+). Benzoyl amide: EA calculated for $C_{27}H_{30}ClF_3N_3O_6$: C, 61.42; H, 5.73; N, 7.96. Found: C, 61.25; H, 5.79; N, 7.69. MS(FD) m/z 528 (M+).

Example 20

1-(3-Carboxypropyl)-Isoxazolo[3,4-c]-1,2-Dihydro-3-Methyl-6-Chloroquinolin-2-one Methyl-N-(3-[2-chloro-6-fluorophenyl]-5-methylisoxazol-4-oyl)-4-aminobutanoate (1.54 g, 4.35 mmol) was converted to 1.15 g of the title compound by the procedure of Example 1 except that the reaction time was 3 hours. (82%). MS(FD) m/z 320 (M+). IR(KBr) 3145, 2925, 1740, 1732, 1651, 1627, 1598 cm$^{-1}$.

Example 21

1-(4-Carboxybutyl)-Isoxazolo[3,4-c]-1,2-Dihydro-3-Methyl-6-Chloroquinolin-2-one

Methyl-N-(3-[2-chloro-6-fluorophenyl]-5-methylisoxazol-4-oyl)-5-aminopentanoate (200 mg, 0.542 mmol) was converted to 180 mg of the title compound by the procedure of Example 20. (100%). EA calculated for $C_{16}H_{15}ClN_2O_4$: C, 57.41; H, 4.52; N, 8.37. Found: C, 57.43; H, 4.53; N, 8.08. MS(FD) m/z 334.1 (M+).

Example 22

1-(5-Carboxypentyl)-Isoxazolo[3,4-c]-1,2-Dihydro-3-Methyl-6-Chloroquinolin-2-one Methyl-N-(3-[2-chloro-6-fluorophenyl]-5-methylisoxazol-4-oyl)-6-aminohexanoate (735 mg, 1.92 mmol) was converted to 499 mg of the title compound by the procedure of Example 21. (74%). EA calculated for $C_{17}H_{17}ClN_2O_4$: C, 58.54; H, 4.91; N, 8.03. Found: C, 58.51; H, 4.99; N, 7.89. MS(FD) m/z 348 (M+).

Example 23

1-(6-Carboxyhexyl)-Isoxazolo[3,4-c]-1,2-Dihydro-3-Methyl-6-Chloroquinolin-2-one

Methyl-N-(3-[2-chloro-6-fluorophenyl]-5-methylisoxazol-4-oyl)-7-aminoheptanoate (1.49 g, 3.75 mmol) was converted to 1.07 g of the title compound by the procedure of Example 21. (79%). EA calculated for $C_{18}H_{19}ClN_2O_4$: C, 59.59; H, 5.28; N, 7.72. Found: C, 59.66; H, 5.49; N, 7.64. MS(FD) m/z 362 (M+).

Example 24

1-(4-Oxo-4-(3,4,5-Trimethoxyphenylamino)butyl)-Isoxazolo[3,4-c]-1,2-Dihydro-3-Methyl-6-Chloroquinolin-2-one 5-(Isoxazolo[3,4-c]-1,2-Dihydro-3-Methyl-6-Chloroquinolin-2-on-1-yl)butanoic Acid and 3,4,5-trimethoxy-aniline were converted to the title compound by the procedure of Example 26 to give 67 mg. (88%). EA calculated for $C_{24}H_{24}ClN_3O_6$: C, 59.32; H, 4.98; N, 5.12. Found: C, 59.52; H, 5.12; N, 8.41. MS(FD) m/z 484.9 (M–H).

Example 25

1-(4-Oxo-4-(3,4,5-Trimethoxybenzylamino)butyl)-Isoxazolo[3,4-c]-1,2-Dihydro-3-Methyl-6-Chloroquinolin-2-one 5-(Isoxazolo[3,4-c]-1,2-Dihydro-3-Methyl-6-Chloroquinolin-2-on-1-yl)butanoic Acid and 3,4,5-trimethoxybenzylamine were converted to the title compound by the procedure of Example 26 to give 37 mg. (47%). EA calculated for $C_{24}H_{24}ClN_3O_6$: C, 60.06; H, 5.24. Found: C, 60.20; H, 5.49. MS(FD) m/z 498.9 (M–H).

Example 26

1-(5-Oxo-5-(3,4,5-Trimethoxyphenylamino)pentyl)-Isoxazolo[3,4-c]-1,2-Dihydro-3-Methyl-6-Chloroquinolin-2-one 1-(4-Carboxybutyl)-isoxazolo[3,4-c]-1,2-dihydro-3-methyl-6-chloroquinolin-2-one (46 mg, 0.137 mmol) was dissolved in 3 mL of dry dichloromethane and stirred at room temperature under nitrogen. 1-Ethyl-3-[3-(dimethylamino)-propyl]carbodiimide hydrochloride (EDCI, 26 mg, 0.137 mmol) was added followed by 3,4,5-trimethoxyaniline (25 mg, 0.137 mmol) and the resulting mixture was stirred for about 18 hours. TLC (ethyl acetate) indicated the reaction was not substantially complete therefore a catalytic amount of dimethylaminopyridine was added and the reaction was allowed to stir for about 18 hours. The reaction was diluted with ethyl acetate and washed three times each with 1N aqueous hydrochloric acid, sodium bicarbonate, brine, dried over sodium sulfate, filtered, and the ethyl acetate removed to give 41 mg of the title compound. (60%). EA calculated for $C_{25}H_{26}ClN_3O_6$: C, 60.06; H, 5.24; N, 8.41. Found: C, 59.94; H, 5.47; N, 8.14. MS(FD) m/z 498.9 (M–H).

Example 27

1-(5-Oxo-5-(3,4,5-Trimethoxybenzylamino)pentyl)-Isoxazolo(3,4-c]-1,2-Dihydro-3-Methyl-6-Chloroquinolin-2-one 1-(4-Carboxybutyl)isoxazolo[3,4-c]-1,2-dihydro-3-methyl-6-chloroquinolin-2-one (40 mg, 0.119 mmol) was suspended in 3 mL of dry dichloromethane and stirred at room temperature under nitrogen. EDCI (23 mg, 0.119 mmol) was added and the reaction went into solution. 3,4,5-Trimethoxybenzylamine (23.6 mg, 0.119 mmol) and a catalytic amount of DMAP was then added and the resulting mixture was stirred for about 18 hours. TLC (ethyl acetate) indicated the reaction was substantially complete. The reaction was diluted with ethyl acetate and washed three times each with 1N aqueous hydrochloric acid, sodium bicarbonate, brine, dried over sodium sulfate, filtered, and the ethyl acetate removed to give 43 mg of the title compound. (70%). EA calculated for $C_{26}H_{26}ClN_3O_6$: C, 60.76; H, 5.49; N, 8.18. Found: C, 60.89; H, 5.66; N, 7.93. MS(FD) m/z 512.8 (M–H).

Example 28

1-(6-Oxo-6-(3,4,5-Trimethoxyphenylamino)hexyl)-Isoxazolo[3,4-c]-1,2-Dihydro-3-Methyl-6-Chloroquinolin-2-one 5-(Isoxazolo[3,4-c]-1,2-Dihydro-3-Methyl-6-Chloroquinolin-2-on-1-yl)hexanoic acid and 3,4,5-trimethoxy-aniline were converted to the title compound by the procedure of Example 26 to give 56 mg. (77%). EA calculated for $C_{26}H_{28}ClN_3O_6$: C, 60.76; H, 5.49; N, 8.17. Found: C, 60.18; H, 5.34; N, 7.82. MS(FD) m/z 513.0 (M–H).

Example 29

1-(6-Oxo-6-(3,4,5-Trimethoxybenzylamino)hexyl)-Isoxazolo[3,4-c]-1,2-Dihydro-3-Methyl-6-Chloroquinolin-2-one 5-(Isoxazolo[3,4-c]-1,2-Dihydro-3-Methyl-6-Chloroquinolin-2-on-1-yl)hexanoic acid and 3,4,5-trimethoxy-aniline were converted to the title compound by the procedure of Example 26 to give 63 mg. (83%). EA calculated for $C_{27}H_{30}ClN_3O_6$: C, 61.42; H, 5.73; N, 7.96. Found: C, 61.32; H, 5.67; N, 7.68. MS(FD) m/z 527.0 (M–H).

Example 30

1-(7-Oxo-7-(3,4,5-Trimethoxyphenylamino)heptyl)-Isoxazolo[3,4-c]-1,2-Dihydro-3-Methyl-6-Chloroquinolin-2-one 5-(Isoxazolo[3,4-c]-1,2-Dihydro-3-Methyl-6-Chloroquinolin-2-on-1-yl)heptanoic acid and 3,4,5-trimethoxyaniline were converted to the title compound by the procedure of Example 26 to give 52 mg. (71%). EA calculated for $C_{27}H_{30}ClN_3O_6$: C, 61.42; H, 5.73; N, 7.96. Found: C, 61.34; H, 5.82; N, 7.68. MS(FD) m/z 526.9 (M–H).

Example 31

1-(7-Oxo-7-(3,4,5-Trimethoxybenzylamino)heptyl)-Isoxazolo[3,4-c]-1,2-Dihydro-3-Methyl-6-Chloroquinolin-2-one 5-(Isoxazolo[3,4-c]-1,2-Dihydro-3-Methyl-6-Chloroquinolin-2-on-1-yl)heptanoic Acid and 3,4,5-trimethoxybenzylamine were converted to the title compound by the procedure of Example 26 to give 69 mg. (92%). EA calculated for $C_{28}H_{32}ClN_3O_6$: C, 62.05; H, 5.95; N, 7.75. Found: C, 61.78; H, 5.82; N, 7.49. MS(FD) m/z 541 (M–H).

The compounds of the invention are inhibitors of MRP1. Thus, the compounds of the invention may be used to inhibit any neoplasm having intrinsic and/or acquired resistance, conferred in part or in total by MRP1, to an oncolytic or oncolytics. In other words, treatment of such a neoplasm with an effective amount of a compound of this invention will cause the neoplasm to be more sensitive to chemotherapy that was rendered less efficacious by MRP1.

Vincristine, epirubicin, daunorubicin, doxorubicin, and etoposide are oncolytics that are substrates of MRP1. See Cole, et. al., "Pharmacological Characterization of Multidrug Resistant MRP-transfected Human Tumor Cells", *Cancer Research*, 54:5902–5910, 1994. Since MRP1 is ubiquitous in mammals, particularly humans, Nooter, K, et. al., "Expression of the Multidrug Resistance-Associated Protein (MRP) Gene in Human Cancers", *Clin. Can. Res.*, 1:1301–1310, (1995), chemotherapy whose goal is to inhibit a neoplasm employing any of those agents has the potential to be rendered less efficacious by MRP1. Thus, neoplasms of the bladder, bone, breast, lung(small-cell), testis, and thyroid and more specific types of cancer such as acute lymphoblastic and myeloblastic leukemia, Wilm's tumor, neuroblastoma, soft tissue sarcoma, Hodgkin's and non-Hodgkin's lymphomas, and bronchogenic carcinoma may be inhibited with a combination of one or more of the above oncolytics and a compound of this invention.

The biological activity of the compounds of the present invention was evaluated employing an initial screening assay which rapidly and accurately measured the activity of the tested compound in inhibiting MRP1 or MDR1. Assays useful for evaluating this reversing capability are well known in the art. See, e.g., T. McGrath, et al., *Biochemical Pharmacology*, 38:3611, 1989; D. Marquardt and M. S. Center, *Cancer Research*, 52:3157, 1992; D. Marquardt, et al., *Cancer Research*, 50:1426, 1990; and Cole, et. al., "Pharmacological Characterization of Multidrug Resistant MRP-transfected Human Tumor Cells", *Cancer Research*, 54:5902–5910, 1994.

Assay for Reversal of MRP1-Mediated Doxorubicin Resistance and MDR1-Mediated Vincristine Resistance: HL60/ADR and HL60/VCR are continuous cell lines, which were selected for doxorubicin and vincristine resistance, respectively, by culturing HL60, a human acute myeloblastic leukemia cell line, in increasing concentrations of doxorubicin or vincristine until a highly resistant variant was attained.

HL60/ADR and HL60/VCR cells were grown in RPMI 1640 (Gibco) containing 10% fetal bovine serum (FBS) and 250 $\mu$g/ml GENTAMICIN™ (Sigma). Cells were harvested; washed twice with assay medium (same as culture media); counted; and diluted to $2 \times 10^5$ cells/ml in assay medium. Fifty microliters of cells were aliquoted into wells of a 96 well tissue culture plate. One column of each 96 well plate served as a negative control and received assay medium containing no cells.

Test compounds and reference compounds were dissolved in dimethyl sulfoxide (DMSO) at a concentration of 5 mM. Samples were diluted to 20 $\mu$M in assay medium and 25 $\mu$l of each test compound was added to 6 wells. Assay standards were run in quadruplicate. Twenty-five microliters of 0.4% DMSO was added to four wells as a solvent control. Assay media was added to all wells to achieve a final volume of 100 $\mu$l per well.

The plates were incubated at 37° C. for 72 hours in a humidified incubator with a 5% carbon dioxide atmosphere. Cell viability and vitality was measured by oxidation of a tetrazolium salt suing standard conditions. The plates were incubated for 3 hours at 37° C. Absorbance was determined at 490 nm using a microtitre plate reader.

The ability of a test compound to reverse the resistance of HL60/ADR and HL60/VCR cells to doxorubicin was determined by comparison of the absorbance of the wells containing a test compound in addition to the oncolytic (doxorubicin) with the absorbance of wells containing the oncolytic without a test compound. Controls were used to eliminate background and to ensure the results were not artifactual. The results of the assay are expressed as percent inhibition of cell growth. The oncolytic alone at the tested concentration does not usually inhibit the growth of HL60/ ADR or HL60/ VCR cells.

Representative compounds of formula I demonstrated a significant effect in reversing the MRP1 multiple drug resistance. Many of the compounds showed very significant enhancement of activity in combination with the oncolytic agent as opposed to the oncolytic agent alone. In addition, a large majority of the compounds tested displayed a significant degree of selective inhibition of the HL60/ ADR cell line over the HL60/ VCR cell line.

When administering an oncolytic in practicing the methods of this invention, the amount of oncolytic employed will be variable. It should be understood that the amount of the oncolytic actually administered will be determined by a physician, in the light of the relevant circumstances, including the condition to be treated, the chosen route of administration, the actual oncolytic administered, the age, weight, and response of the individual patient (mammal), and the severity of the patient's symptoms. Of course, the amount of oncolytic administered should be decided and closely monitored by that patient's physician. After deciding on the oncolytic or oncolytics to employ, "The Physician's Desk Reference®", published by Medical Economics Company at Montvale, N.J. 07645–1742, is a helpful resource to the physician in deciding on amounts of the oncolytic to administer and is updated annually.

Preferred formulations, and the methods of this invention employing those formulations, are those which do not contain an oncolytic. Thus, it is preferred to administer the compounds of this invention separately from the oncolytic. The oncolytics mentioned in this specification are commercially available and may be purchased in pre-formulated forms suitable for the methods of this invention.

The compounds of formula I alone, or optionally in combination with an oncolytic, are usually administered in the form of pharmaceutical formulations. These formulations can be administered by a variety of routes including oral, rectal, transdermal, subcutaneous, intravenous, intramuscular, and intranasal. Such formulations are prepared in a manner well known in the pharmaceutical art and comprise at least one active compound of formula I.

The present invention also includes methods employing pharmaceutical formulations which contain, as the active ingredient, the compounds of formula I, and optionally an oncolytic, associated with pharmaceutical carriers. In making the formulations of the present invention the active ingredient(s) is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound(s) to provide the appropriate particle size prior to combining with the other ingredients. If the active compound(s) is substantially insoluble, it ordinarily is milled to a particle size of less than 200 mesh. If the active compound(s) is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The formulations of the invention can be formulated so as to provide quick, sustained or delayed release of the active ingredient after administration to the patient by employing procedures known in the art.

The formulations are preferably formulated in a unit dosage form, each dosage containing from about 5 to about 100 mg, more usually about 10 to about 30 mg, of each active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds of formula I are effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid formulations such as tablets the principal active ingredient(s) is mixed with a pharmaceutical excipient to form a solid preformulation composition containing a homogeneous mixture of a compound of the present invention. When referring to these preformulation compositions as homogeneous, it is meant that the active ingredient(s) is dispersed evenly throughout the formulation so that the formulation may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The novel formulations which are liquid forms may be incorporated for administration orally or by injection and include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Formulations for inhalation or insufflation include solutions and suspensions in pharmaceutical, aqueous or organic solvents, or mixtures thereof, and powders. The liquid or solid formulations may contain suitable pharmaceutical excipients as described supra. Preferably the formulations are administered by the oral or nasal respiratory route for local or systemic effect. Compositions in preferably pharmaceutical solvents may be nebulized by use of inert gases. Nebulized solutions may be breathed directly from the nebulizing device or the nebulizing device may be attached to a face mask, tent, or intermittent positive pressure breathing machine. Solution, suspension, or powder formulations may be administered, preferably orally or nasally, from devices which deliver the formulation in an appropriate manner.

The following formulation examples are illustrative only and are not intended to limit the scope of the invention in any way. "Active Ingredient(s)" means a compound according to formula I or a pharmaceutical salt or solvate thereof optionally with one or more oncolytics.

Formulation Example 1

Hard gelatin capsules containing the following ingredients are prepared:

| Ingredient | Quantity (mg/capsule) |
| --- | --- |
| Active Ingredient(s) | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient(s) | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient(s) | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient(s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Active Ingredient(s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient(s) | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient(s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Active Ingredient(s) | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
|---|---|
| Active Ingredient(s) | 250.0 mg |
| Isotonic saline | 1000 ml |

Formulation Example 10

A topical formulation may be prepared as follows:

| Ingredient | Quantity |
|---|---|
| Active Ingredient(s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
|---|---|
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical formulation to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A compound of formula I:

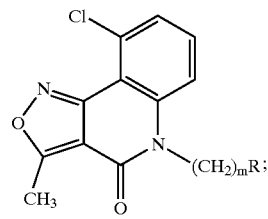

where:
m is an integer from 1 to 6;
R is $COR^1$, amino, NH-Pg, or $NHCOR^2$;
$R^1$ is hydroxy, $C_1$–$C_6$ alkoxy, or $NR^3R^4$;
Pg is an amino protecting group;
$R^2$ is $C_1$–$C_6$ alkyl, substituted $C_1$–$C_4$ alkyl, aryl, or substituted aryl;
$R^3$ is independently at each occurrence hydrogen or $C_1$–$C_6$ alkyl;
$R^4$ is $C_1$–$C_6$ alkyl, norbornan-2-yl, aryl, substituted aryl, or $CH_2CH(CH_3)$phenyl; and
n is 0, 1, or 2; or a non-toxic pharmaceutical salt or solvate thereof.

2. The compound according to claim 1 where m is an integer from 2 to 6 and R is selected from: t-butyloxycarbonylamino, trifluoroacetylamino, 3,4,5-trimethoxybenzoylamino, 3,4,5-trimethoxyanilinylcarboxy, 3,4,5-trimethoxybenzylaminylcarboxy; or a non-toxic pharmaceutical salt or solvate thereof.

3. A method of inhibiting MRP1 in a mammal which comprises administering to a mammal in need thereof an effective amount of a compound of formula I:

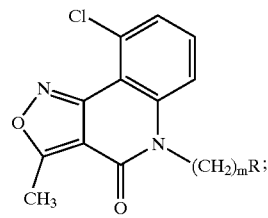

where:

m is an integer from 1 to 6;
R is $COR^1$, amino, NH-Pg, or $NHCOR^2$;
$R^1$ is hydroxy, $C_1$–$C_6$ alkoxy, or $NR^3R^4$;
Pg is an amino protecting group;
$R^2$ is $C_{1-C6}$ alkyl, substituted $C_1$–$C_4$ alkyl, aryl, or substituted aryl;
$R^3$ is independently at each occurrence hydrogen or $C_1$–$C_6$ alkyl;
$R^4$ is $C_1$–$C_6$ alkyl, norbornan-2-yl, aryl, substituted aryl, or $CH_2CH(CH_3)$phenyl; and
n is 0, 1, or 2; or a non-toxic pharmaceutical salt or solvate thereof.

4. The method according to claim 3 where the mammal is a human.

5. The method according to claim 4 where the compound of formula I is a compound where m is an integer from 2 to 6 and R is selected from: t-butyloxycarbonylamino, trifluoroacetylamino, 3,4,5-trimethoxybenzoylamino, 3,4,5-trimethoxyanilinylcarboxy, 3,4,5-trimethoxybenzylaminylcarboxy; or a non-toxic pharmaceutical salt or solvate thereof.

6. A pharmaceutical formulation comprising a compound of formula I:

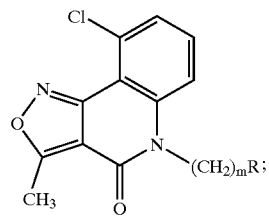

where:

m is an integer from 1 to 6;
R is $COR^1$, amino, NH-Pg, or $NHCOR^2$;
$R^1$ is hydroxy, $C_1$–$C_6$ alkoxy, or $NR^3R^4$;
Pg is an amino protecting group;
$R^2$ is $C_1$–$C_6$ alkyl, substituted $C_1$–$C_4$ alkyl, aryl, or substituted aryl;
$R^3$ is independently at each occurrence hydrogen or $C_1$–$C_6$ alkyl;
$R^4$ is $C_1$–$C_6$ alkyl, norbornan-2-yl, aryl, substituted aryl, or $CH_2CH(CH_3)$phenyl; and
n is 0, 1, or 2; or a non-toxic pharmaceutical salt or solvate thereof; in combination with one or more pharmaceutical carriers, diluents, or excipients thereof.

* * * * *